United States Patent
Billich et al.

(10) Patent No.: US 6,346,626 B1
(45) Date of Patent: Feb. 12, 2002

(54) CHROMANONE AND THIOCHROMANONE COMPOUNDS

(75) Inventors: Andreas Billich, Mödling; Peter Nussbaumer, Maria Enzersdorf; Erwin Schreiner; Ingeborg Schuster, both of Vienna, all of (AT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/680,887

(22) Filed: Oct. 6, 2000

Related U.S. Application Data

(63) Continuation of application No. PCT/EP99/02349, filed on Apr. 7, 1999.

(30) Foreign Application Priority Data

May 4, 1998 (GB) ............................................... 9807779

(51) Int. Cl.[7] ..................... C07D 311/04; C07D 335/04; A61K 31/352; A61K 31/38

(52) U.S. Cl. ......................... 549/23; 549/401; 514/436; 514/460

(58) Field of Search ................... 549/401, 23; 514/432, 514/460

(56) References Cited

U.S. PATENT DOCUMENTS

| | | | | |
|---|---|---|---|---|
| 4,105,778 A | * | 8/1978 | Philipp et al. | 424/275 |
| 4,415,741 A | * | 11/1983 | Kabbe et al. | 549/345 |
| 4,900,727 A | * | 2/1990 | Kattige et al. | 514/212 |
| 5,025,031 A | | 6/1991 | Lo et al. | 514/399 |
| 5,194,446 A | | 3/1993 | Lo et al. | 514/494 |
| 5,273,993 A | | 12/1993 | Lo et al. | 514/400 |
| 5,556,847 A | | 9/1996 | Johnson et al. | 514/178 |
| 5,567,831 A | | 10/1996 | Li | 554/43 |
| 5,763,492 A | | 6/1998 | Johnson et al. | 514/603 |
| 6,028,088 A | * | 2/2000 | Pershadsingh et al. | 514/369 |
| 6,218,427 B1 | * | 4/2001 | Ishikzuka et al. | 514/456 |

FOREIGN PATENT DOCUMENTS

| | | |
|---|---|---|
| EP | 0111746 B1 | 6/1984 |
| EP | 0 125 195 | 11/1984 |
| EP | 0 323 745 | 7/1989 |
| EP | 0 403 185 | 12/1990 |
| EP | 0588137 A1 | 3/1994 |
| WO | 93/05064 | 3/1993 |
| WO | 95/26717 | 10/1995 |
| WO | 97/09324 | 3/1997 |
| WO | 97/30041 | 8/1997 |
| WO | 97/32872 | 9/1997 |

OTHER PUBLICATIONS

Ahmed et al., "Molecular Modelling of Oestrone Sulphatase Inhibitors," Pharm. Pharmacol. Commun., vol. 4, pp. 481–483 (1998).

Anderson et al., "Estrone Sulfatase: Probing Structural Requirements for Substrate and Inhibitor Recognition," Biochemistry, vol. 36, pp. 2586–2594 (1997); Supplemental Correction attached.

Corral et al., "Sintesis Y Activida Anticolesterasica de una Serie de N,N–Dimetilsulfamatos de Arilo," Anales de Fisica Y Quimica, pp. 341–344, (1964) (English abstract attached).

Derwent Abstract 90–301419/40 of JO 2212–836–A, 8/24/90).

Howarth et al., "Estrone Sulfamates: Potent Inhibitors of Estrone Sulfatase with Therapeutic Potential," J. Med. Chem., vol. 37, pp. 219–221 (1994).

Li et al., "Development of potent non–estrogenic estrone sulfatase inhibitors," Steroids, vol. 63, pp. 425–432 (1998).

Li et al., "Memory enhancement mediated by the steroid sulfatase inhibitor (pO–Sulfamoyl)–N–tetradecanoyl tyramine," Life Sciences, Vo. 60(3), p. PL 45–51 (1997).

(List continued on next page.)

*Primary Examiner*—Floyd D. Higel
*Assistant Examiner*—Kamal Saeed
(74) *Attorney, Agent, or Firm*—Carol A. Loeschorn

(57) ABSTRACT

The invention concerns the compounds of formula I

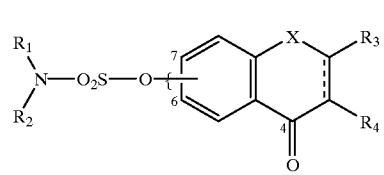

wherein $R_1$ and $R_2$ independently are hydrogen, acyl, alkoxycarbonyl or alkyl; either the sulfamoyloxy side chain is bound to the 6 position;

$R_3$ is alkyl; alkenyl; alkinyl; a cycloalkyl moiety optionally substituted by alkyl, alkoxy or halogen; arylalkenyl; arylalkinyl; acyl; cycloalkylalkyl; 3-oxo-2-oxacamphanyl; or is 6,6-dimethylbicyclo[3.1.1]hept-2-en-2-yl; and $R_4$ is hydrogen; alkyl; hydroxy; or alkoxy;

or the sulfamoyloxy side chain is bound to the 7 position;

$R_3$ has the significance indicated above for $R_4$; and $R_4$ has the significance indicated above for $R_3$;

X is O or S; and the symbol - - - is a single or a double bond;

in free form or salt form.

They can be prepared by sulfamoylation of corresponding hydroxylated compounds, by reduction and/or by N-substitution.

They are indicated for use as pharmaceuticals, particularly in the prophylactic or curative treatment of illnesses responsive to steroid sulfatase inhibition.

9 Claims, No Drawings

OTHER PUBLICATIONS

Li et al., "Synthesis and Sulfatase Inhibitory activities of non–steroidal Estrone Sulfatase Inhibitors," J. Steroid Biochem. Molec. Biol., vol. 59(1), pp. 41–48 (1996).

Purohit et al., "In Vivo Activity of 4–methylcoumarin–7–O–Sulfamate, a Nonsteroidal, Non-estrogenic Steroid Sulfatase Inhibitor," Cancer Research, vol. 56, pp. 4950–4955 (1996).

Purohit et al., "Oestrogen Sulphatase Activity in Hormone–Dependent and Hormone–independent Breast–Cancer Cells: Modulation by Steroidal and Non–Steroidal Therapeutic Agents," Int. J. Cancer, vol. 50, pp. 901–905 (1992).

Reed et al., "Steroid Sulphatase Inhibitors: a New Endocrine Therapy," Drugs of the Future, vol. 19(7), pp. 673–680 (1994).

Rhodes et al., "Enhanced plasma DHEAS, brain acetylcholine and memory mediated by steroid sulfatase inhibition," Brain Research, vol. 773, pp. 28–32 (1997).

Selcer et al., "Inhibition of Estrone Sulfatase and Proliferation of Human Breast Cancer Cells by Nonsteroidal (p–O–Sulfamoyl)–N–alkanoyl Tyramines," Cancer Research, vol. 57, pp. 702–707 (1997).

Smith et al., "Effect of Anti–Inflammatory Drugs on Lysosomes and Lysosomal Enzymes from Rat Liver," Biochemical Pharmacology, vol. 25, pp. 2171–2177.

Ucelay et al., "On the Mechanism of the Pharmacological Activity of the New Nonsteroidal Antiiflammatory Agent 4'–Acetamidophenyl–2–(5'–p–Toluyl–1'– methylpyrrole)acetate,".

Woo et al., "Active Site Directed Inhibition of Estrone Sulfatase by Nonsteroidal Coumarin Sulfatames," J. Med. Chem., vol. 39, p. 1349–1351 (1996).

Woo et al., "Steroidal and Nonsteroidal Sulfamates as Potent Inhibitors of Steroid Sulfatase," J. Med. Chem., vol. 41, pp. 1068–1083 (1998).

* cited by examiner

CHROMANONE AND THIOCHROMANONE COMPOUNDS

This is a continuation of International Application No. PCT/EP99/02349, filed on Apr. 7, 1999, the contents of which are incorporated herein by reference.

The invention relates to chromanone and thiochromanone derivatives. It concerns the compounds of formula I

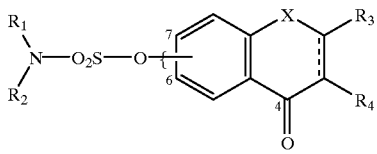

wherein
- $R_1$ and $R_2$ independently are hydrogen, acyl, alkoxycarbonyl or alkyl;
- either the sulfamoyloxy side chain is bound to the 6 position;
- $R_3$ is alkyl; alkenyl; alkinyl; a cycloalkyl moiety optionally substituted by alkyl, alkoxy or halogen; arylalkenyl; arylalkinyl; acyl; cycloalkylalkyl; 3-oxo-2-oxacamphanyl; or is 6,6-dimethylbicyclo[3.1.1]hept-2-en-2-yl; and
- $R_4$ is hydrogen; alkyl; hydroxy; or alkoxy;
- or the sulfamoyloxy side chain is bound to the 7 position;
- $R_3$ has the significance indicated above for $R_4$; and
- $R_4$ has the significance indicated above for $R_3$;
- X is O or S; and the symbol --- is a single or a double bond;

in free form or salt form; hereinafter briefly named "the compounds of the invention".

A compound of formula I may be present in free, i.e. neutral or base, form or, where such forms exist, in salt, particularly acid addition salt form. A compound of formula I in free form may be converted into a salt form in conventional manner and vice-versa.

The sulfamoyloxy side chain is bound preferably to the 6 position.

Acyl preferably is the residue of a carboxylic acid, in particular of an alkyl, arylalkyl or aryl carboxylic acid. It preferably is alkylcarbonyl of altogether 2 to 5 carbon atoms, it especially is acetyl. Alkoxycarbonyl preferably is of altogether 2 to 5 carbon atoms, it especially is methoxycarbonyl. Alkyl as a moiety $R_1$ or $R_2$ or as part of a substituent preferably is of 1 to 5 carbon atoms, it especially is methyl. Alkyl as a moiety $R_3$ or $R_4$ preferably is of 1 to 12 carbon atoms, it especially is methyl, ethyl or t-butyl, particularly t-butyl. Alkenyl preferably is of 2 to 5 carbon atoms, it conveniently is ethenyl. Alkinyl preferably is of 2 to 5 carbon atoms, it conveniently is ethinyl.

A cycloalkyl moiety may be monocyclic or polycyclic. When it is monocyclic, it preferably is of 3 to 12 carbon atoms, it especially is cyclopropyl, cyclopentyl or cyclohexyl; when it is polycyclic, it preferably is adamantyl, especially 1-adamantyl; nor-adamantyl; or bicyclo[2.2.2]oct-1-yl. When cycloalkyl is substituted, it preferably is substituted by alkyl.

Arylalkenyl preferably is of 2 to 4 carbon atoms in the alkenylene part thereof. It preferably is 2-phenylethenyl, preferably in the trans configuration. Arylalkinyl preferably is of 2 to 4 carbon atoms in the alkinylene part thereof.

Cycloalkylalkyl preferably is of 1 to 4, especially 1 carbon atom in the alkylene part thereof. The cycloalkyl part thereof may be monocyclic or polycyclic; when it is monocyclic, it preferably is of 3 to 12 carbon atoms, it especially is cyclopentyl or cyclohexyl; when it is polycyclic, it preferably is bicyclo[2.2.1]hept-2-yl.

Alkoxy preferably is of 1 to 4 carbon atoms, it especially is methoxy. Halogen is fluorine, chlorine or bromine, preferably chlorine.

$R_1$ and $R_2$ preferably are hydrogen or alkyl, especially hydrogen. They preferably are identical. $R_3$ preferably is alkyl or cycloalkyl. $R_4$ preferably is hydrogen. X conveniently is O. The symbol --- preferably is a double bond.

In a preferred subgroup of compounds of the invention $R_1$ and $R_2$ are identical and are hydrogen or methyl, and $R_3$ is t-butyl; cyclopentyl; cyclohexyl; adamantyl; bicyclo[2.2.1]hept-2-ylmethyl; nor-adamantyl; 4-pentylbicyclo[2.2.2]oct-1-yl; 6,6-dimethylbicyclo[3.1.1]hept-2-en-2-yl; camphanyl; styryl; 2,2,3,3-tetramethylcyclopropyl; or alkyl of 1 to 4 carbon atoms.

In a further preferred subgroup $R_1$, $R_2$ and $R_4$ are hydrogen; the sulfamoyloxy side chain is bound to the 6 position; $R_3$ is a bulky moiety selected from the significances indicated above for $R_3$, preferably branched alkyl of 4 to 12 carbon atoms, such as tert-butyl; a monocyclic cycloalkyl moiety of 5 to 12 carbon atoms or a bi- or tricyclic cycloalkyl moiety of 6 to 10 carbon atoms, each optionally mono- or independently di- or independently trisubstituted by alkyl of 1 to 5 carbon atoms; 3-oxo-2-oxacamphanyl; or 6,6-dimethyl-bicyclo[3.1.1]hept-2-en-2-yl; and X and the symbol --- are as defined above.

A further preferred subgroup of compounds of the invention is the compounds of formula Ip

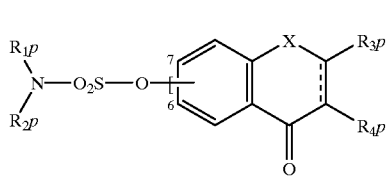

wherein

- $R_{1p}$ and $R_{2p}$ independently are hydrogen or alkyl;
- either the sulfamoyloxy side chain is bound to the 6 position,
- $R_{3p}$ with the exception of 3-oxo-2-oxacamphanyl has the significance indicated above for $R_3$, and
- $R_{4p}$ is hydrogen;
- or the sulfamoyloxy side chain is bound to the 7 position,
- $R_{3p}$ is hydrogen, and
- $R_{4p}$ with the exception of 3-oxo-2-oxacamphanyl has the significance indicated above for $R_3$; and
- X and the the symbol --- are as defined above;

in free form or salt form.

A further preferred subgroup of compounds of the invention is the compounds of formula Is

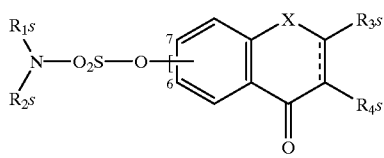

wherein

R$_{1s}$ is hydrogen, methyl, acetyl or methoxycarbonyl;

R$_{2s}$ is hydrogen or methyl;

either the sulfamoyloxy side chain is bound to the 6 position,

R$_{3s}$ is alkyl of 1 to 12 carbon atoms; a monocyclic cycloalkyl moiety of 3 to 12 carbon atoms optionally substituted by methyl; 1-adamantyl; nor-adamantyl; 4-pentylbicyclo[2.2.2]oct-1-yl; 2-phenylethenyl; bicyclo[2.2.1]hept-2-ylmethyl; 3-oxo-2-oxacamphanyl; or 6,6-dimethylbicyclo[3.1.1]hept-2-en-2-yl, and R$_{4s}$ is hydrogen;

or the sulfamoyloxy side chain is bound to the 7 position,

R$_{3s}$ is hydrogen, and

R$_{4s}$ is cycloalkyl of 5 to 7 carbon atoms; and

X and the symbol --- are as defined above;

in free form or salt form.

The invention also provides a process for the preparation of the compounds of the invention comprising a) sulfamoylating the compounds of formula II

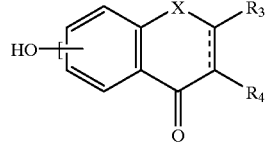

wherein R$_3$, R$_4$, X and the symbol --- are as defined above; or b) for the preparation of the compounds of formula Ia

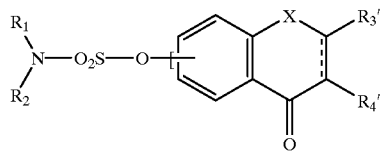

wherein

X, R$_1$, R$_2$ and the symbol --- are as defined above and R$_3$' and R$_4$' with the exception of alkenyl, alkinyl, arylalkenyl, arylalkinyl and 6,6-dimethylbicyclo[3.1.1]hept-2-en-2-yl have the significance indicated above for, respectively, R$_3$ and R$_4$, reducing the corresponding compounds of formula Ib

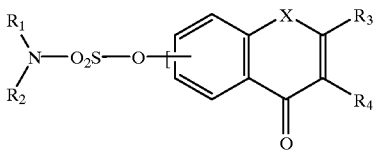

wherein the substituents are as defined above; or c) for the preparation of the compounds of formula I wherein at least one of R$_1$ and R$_2$ is alkyl, acyl or alkoxycarbonyl, N-substituting the compounds of formula I wherein at least one of the substituents R$_1$ and R$_2$ is hydrogen; and recovering the resultant compounds of formula I in free form or salt form.

The process of the invention is carried out in conventional manner.

Process variant a) is performed using standard conditions for sulfamoylation, e.g. by reacting a compound of formula II with:

α) sulfuryl chloride and sodium- or potassium azide to generate corresponding intermediates wherein the hydrogen atom of tho hydroxy group is replaced with a group —SO$_2$N$_3$, which after reduction of the azide group give compounds of formula I wherein R$_1$ and R$_2$ are hydrogen, or β) ClSO$_2$—NCO, followed by aqueous hydrolysis of the resultant intermediates to yield compounds of formula I wherein R$_1$ and R$_2$ are hydrogen, or γ) a compound of formula III

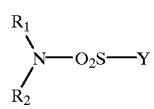

wherein R$_1$ and R$_2$ are as defined above and Y is a leaving group, e.g. halogen, preferably chlorine, in an inert solvent, e.g. dimethylformamide, where convenient with addition of an organic base, such as an organic tertiary amine, or an inorganic base, e.g. an alkali(hydrogen)carbonate or alkali hydride, preferably sodium hydride.

Process variant b) may be performed following standard procedures for hydrogenation of double bonds, e.g. catalytically, preferably using hydrogen in combination with a hydrogenation catalyst such as Pd, Pt or Rh, most preferably Pd on charcoal. Starting from compounds of formula I wherein R$_3$ is alkenyl alkinyl, arylalkenyl or arylalkynyl, in a first step of the reaction these groups are reduced. The reaction may be stopped at this stage and the double bond in the chromenone ring remain unchanged. Further reduction gives compounds of formula Ia wherein the symbol --- is a single bond.

Process variant c) is performed according to standard procedures for N-substitution by alkylation or acylation, conveniently using alkylhalogenides, -sulfates or -mesylates, preferably alkyl iodides, or acyl- or alkoxycarbonylhalides, preferably chlorides, preferably in the presence of a suitable base, such as an alkali carbonate or alkali hydride, conveniently in an inert and preferably polar solvent such as acetone or dimethylformamide, preferably at temperatures of between about −20° and about 120° C., preferably between room temperature and about 60° C.

The resultant compounds of the invention may be recovered from the reaction mixture and isolated and purified in conventional manner. Isomers, such as enantiomers, may be obtained in conventional manner, e.g. by fractional crystallization or asymmetric synthesis from corresponding asymmetrically substituted, e.g. optically active starting materials.

The starting materials and intermediate compounds are either known or can be prepared according to known methods or analogously as described in the Examples.

Structurally related compounds with a sulfamate group are known from WO 97/32872, cited during the International Phase of the present application, the scope of which has been amended in view thereof.

The following Examples illustrate the invention. All temperatures are in degrees Celsius. The compounds of the invention are in free form unless specified otherwise. The following abbreviations are used:

Ad=1-adamantyl=tricyclo[3.3.1.1$^{3,7}$]dec-1-yl
Cam=1-camphanyl=4,7,7-trimethylbicyclo[2.2.1]hept-1-yl
db=double bond
DMSO=dimethylsulfoxide
mp=melting point
nor-Ad=noradamantyl
sb=single bond
t-=tertiary

EXAMPLE 1

2-t-Butyl-4H-chromen-4-one-6-O-sulfamate
[Process Variant a)]

158 mg sodium hydride (80% in mineral oil) is added to a solution of 400 mg 2-t-butyl-6-hydroxy-4H-chromen-4-one in dry dimethylformamide. After stirring for 30 minutes at room temperature 630 mg amidosulfonyl chloride is added, and stirring is continued for additionally 3 hours. The solvent is distilled off in vacuo and the residue partitioned between water and ethyl acetate. The aqueous layer is extracted with ethyl acetate, and the, organic layers are combined, dried over magnesium sulfate and concentrated in vacuo. The residue is taken up in dichloromethane and passed through a short silica gel column (cyclohexane/ethyl acetate 1/1). The title compound is obtained (colourless crystals; mp 178–180°—from 2-propanol; mp 180°—from toluene).

Analogously as described in Example 1 the following compounds of the invention are prepared:

| Example No. | Position of sulfamoyloxy moiety | R$_1$ | R$_2$ | R$_3$ | R$_4$ | X | --- | mp |
|---|---|---|---|---|---|---|---|---|
| 2 | 6 | H | H | 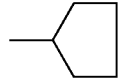 | H | O | db | 158–160° |
| 3 | 6 | H | H | 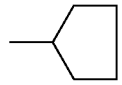 | H | O | sb | 127° |
| 4 | 6 | H | H | 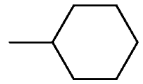 | H | O | db | 170–171° |
| 5 | 6 | H | H | 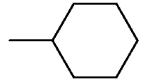 | H | O | sb | 136–138° |
| 6 | 6 | H | H | —CH=CH— (E) 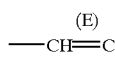 | H | O | db | 185–188° |
| 7 | 6 | H | H | —C(CH$_3$)$_3$ | H | O | sb | 118–120° |
| 8 | 6 | H | H | Ad | H | O | db | 166–168° |
| 9 | 6 | CH$_3$ | CH$_3$ | —C(CH$_3$)$_3$ | H | O | db | 83–85° |
| 10 | 6 | H | H | —(CH$_2$)$_8$—CH$_3$ | H | O | db | 77–80° |

-continued

| Example No. | Position of sulfamoyloxy moiety | R₁ | R₂ | R₃ | R₄ | X | = | mp |
|---|---|---|---|---|---|---|---|---|
| 11 | 6 | H | H | (+)-3-oxo-2-oxa-Cam | H | O | db | 210–212° |
| 12 | 6 | H | H | (−)-3-oxo-2-oxa-Cam | H | O | db | 213–215° |
| 13 | 6 | H | H | Ad | H | O | sb | 192–194° |
| 14 | 6 | H | H | 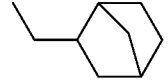 bicyclo-[2.2.1]hept-2-ylmethyl | H | O | db | 165° |
| 15 | 6 | H | H | nor-Ad | H | O | db | 165–167° |
| 16 | 6 | H | H | nor-Ad | H | O | sb | 165–167° |
| 17 | 6 | H | H | 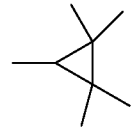 2,2,3,3-tetramethylcyclopropyl | H | O | db | 148° |
| 18 | 6 | H | H | 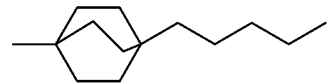 4-pentylbicyclo[2.2.2]-oct-1-yl | H | O | db | 185° |
| 19 | 6 | H | H | —CH₂CH₂CH₃ | H | O | db | 148° |
| 20 | 6 | H | H | 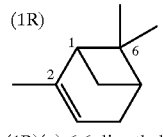 (1R)(−)-6,6-dimethylbicyclo-[3.1.1]hept-2-en-2-yl | H | O | db | 112° |
| 21 | 6 | H | H | —C(CH₃)₃ | H | S | db | 150–153° |
| 22 | 6 | H | H | Ad | H | S | db | 220° |
| 23 | 7 | H | H | H | 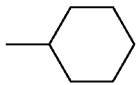 | O | db | 160–163° |
| 24 | 6 | H | H | cyclododecyl | H | O | db | 168–170° |
| 24a | 6 | H | H | 1,1-dimethylnon-1-yl | H | O | db | 122° |

EXAMPLE 25

2-Cyclohexylchroman-4-on-6-O-sulfamate (Process Variant b)

90 mg 2-cyclohexyl-4H-chromen-4-on-6-O-sulfamate (Example 4) is dissolved in ethyl acetate and hydrogenated over palladium (10% on charcoal) at atmospheric pressure and room temperature for 3 hours. The mixture is filtered over silicagel (celite), and the filtrate is evaporated in vacuo. The residue is chromatographed on silica gel (cyclohexane/ ethyl acetate 2/1). The title compound is obtained (colourless crystals; mp 136–138°).

Analogously as described in Example 25 the following compounds of the invention are obtained:

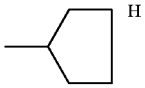

| Example No. | Position of sulfamoyloxy moiety | R₁ | R₂ | R₃ | R₄ | X | = | mp |
|---|---|---|---|---|---|---|---|---|
| 26 | 6 | H | H | 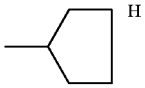 | H | O | sb | 127° |
| 27 | 6 | H | H | —C(CH₃)₃ | H | O | sb | 118–120° |
| 28 | 6 | H | H | Ad | H | O | sb | 192–194° |
| 29 | 6 | H | H | nor-Ad | H | O | sb | 165–167° |

EXAMPLE 30

N-Acetylsulfamic acid 2-(1-adamantyl)-4H-chromen-4-on-6-yl ester (Process Variant c)

100 mg 2-(1-adamantyl)-4H-chromen-4-one-6-O-sulfamate (Example 8) and 32 mg triethylamine are dissolved in dry dichloromethane and treated with 32 mg of acetic anhydride at room temperature. The mixture is stirred 1 hour at room temperature, then poured into aqueous pH 7 buffer solution and extracted with ethyl acetate. The combined organic layers are dried over magnesium sulfate and concentrated in vacuo. The title compound is obtained (viscous gum).

[$^1$H-NMR(DMSO-$d_6$): 7.71 (d, J=2.8 Hz, 1H); 7.59 (d, J=9 Hz, 1H); 7.51 (dd, J=2.8+9 Hz, 1H); 6.10 (s, 1H); 5.77 (s, 1H); 2.06 (br.s, 3H); 1.93 (br.s, 6H); 1.73 (br.s, 6H); 1.69 (s, 3H)].

EXAMPLE 31

N,N-Dimethylsulfamic acid 2-t-butyl-4H-chromen-4-on-6-yl ester (Process Variant c)

52 mg sodium hydride (95%) is added to a solution of 240 mg 2-t-butyl-4H-chromen-4-one-6-O-sulfamate (Example 1) in dry dimethylformamide. The mixture is stirred for 20 minutes at room temperature and then treated with 200 mg of methyl iodide. Stirring is continued for an additional 2 hours, the mixture is poured into aqueous pH 7 buffer solution and extracted with ethyl acetate. The combined organic layers are dried over magnesium sulfate and concentrated in vacuo. The residue is chromatographed on silica gel (cyclohexane/ethyl acetate 5/1). The title compound is obtained (colourless crystals; mp 83–85°).

Analogously as described in Examples 30 and 31 the following compound of the invention is obtained:

| Example No. | Position of sulfa-moyloxy moiety | $R_1$ | $R_2$ | $R_3$ | $R_4$ | X | = | mp |
|---|---|---|---|---|---|---|---|---|
| 32 | 6 | —COOCH$_3$ | H | Ad | H | O | db | amorphous* |

*$^1$H-NMR (DMSO-$d_6$): 7.75 (d, J = 2.7Hz, 1H); 7.63 (d, J = 9Hz, 1H); 7.57 (dd, J = 2.7 + 9Hz, 1H); 6.12 (s, 1H); 3.38 (s, 3H); 2.09 (br.s, 3H); 1.96 (s, 3H); 1.95 (s, 3H); 1.75 (br.s, 3H).

The starting materials can be prepared in the following manner:

A) 6-Hydroxy-2-(2-methylphenyl)-4H-chromen-4-one

6-Benzyloxy-2-(2-methylphenyl)-4H-chromen-4-one (mp 115°) is hydrogenated in ethyl acetate over palladium (10% on charcoal) at atmospheric pressure and room temperature for 1 hour. The mixture is filtered over celite, and the filtrate is evaporated in vacuo. The title compound is obtained (colourless crystals; mp 180°).

B) 2-(1-Adamantyl)-6-hydroxy-4H-chromen-4-one a) 4 g 1-adamantoyl chloride are added to a solution of 1.5 g 2,5-dihydroxyacetophenone in dry pyridine. The mixture is stirred for 18 hours at 40°, poured into water and extracted with ethyl acetate. The combined organic layers are washed 3 times with 1 N aqueous hydrochloric acid and subsequently with aqueous sodium carbonate solution, dried over magnesium sulfate and concentrated in vacuo. The crude product is dissolved in dry dimethylformamide and added dropwise at 5° to a suspension of 330 mg of sodium hydride (80% in mineral oil) in dry dimethylformamide. The cooling bath is removed, and the mixture is stirred for 4 hours at room temperature. Then 1.5 ml of acetic acid and 250 ml of water are added, followed by extraction with ethyl acetate. The combined extracts are dried over magnesium sulfate and evaporated in vacuo. The residue is chromatographed on silica gel (cyclohexane/ethyl acetate 6/1) to remove starting materials and major by-products. Cyclisation of the resultant 1-[5-(1-adamantoyloxy)-2-hydroxyphenyl]-3-(1-adamantyl)-1,3-propandione is achieved by treatment with 20 ml of 32% aqueous hydrochloric acid in methanol/dioxane. 6-(1-adamantoyloxy)-2-(1-adamantyl)-4H-chromen-4-one is obtained:

$^1$H-NMR (CDCl$_3$): 7.81 (d, J=2.7 Hz, 1H), 7.48 (d, J=9 Hz, 1H), 7.35 (dd, J=2.7+9 Hz, 1H), 6.19 (s, 1H), 2.12 (br.s, 12H), 1.97 (s, 3H), 1.95 (s, 3H), 1.78 (s, 12H).

b) 330 mg 6-(1-adamantoyloxy)-2-(1-adamantyl)-4H-chromen-4-one is dissolved in dioxane and treated with 5 ml of 10% aqueous potassium hydroxide solution. The mixture is stirred for 3 hours at room temperature and then poured into 2M aqueous pH 7 buffer solution. Extraction with ethyl acetate yields after drying and evaporation a crude product which is purified by chromatogaphy. The title compound is obtained [colourless crystals; mp 230°(from 2-propanol)].

Analogously the following compounds can be prepared:

6-Hydroxy-2-(2phenylethenyl)-4H-chromen-4-one (mp 217–222°);

2t-butyl-6-hydroxy-4H-chromen-4-one (mp 169–171°);

(+)-6-hydroxy-2-(4,7,7-trimethyl-3-oxo-2-oxa-bicyclo[2.2.1]hept-1-yl)-4H-chromen-4-one (mp 227°);

2-nonyl-6-hydroxy-4H-chromen-4-one (mp 95–97°);

(−)-6-hydroxy-2-(4,7,7-trimethyl-3-oxo-2-oxa-bicyclo[2.2.1]hept-1-yl)-4H-chromen-4-one (mp 232°);

2-(bicyclo[2.2.1]hept-2-ylmethyl)-6hydroxy-4H-chromen-4-one (mp 186°);

6-hydroxy-2-noradamantyl-4H-chromen-4-one (mp 190°);

6-hydroxy-2-(2,2,3,3-tetramethylcyclopropyl)-4H-chromen-4-one (mp 173°);

6-hydroxy-2-(4-pentylbicyclo[2.2.1]oct-1-yl)-4H-chromen-4-one (mp 180–182°);

6-hydroxy-2-propyl-4H-chromen-4-one (mp 150°);

2-{(1R)(−)-6,6-dimethylbicyclo[3.1.1]hept-2-en-2-yl}-6-hydroxy-4H-chromen-4-one (mp 155–158°);

2-cyclododecyl-6-hydroxy-4H-chromen-4-one (mp 168–170°);

2-cyclohexyl-6-hydroxy-4H-chromen-4-one

[$^1$H-NMR (DMSO-$d_6$): 10.72 (br.s, 1H); 7.98 (s, 1H); 7.89 (d, J=8.7 Hz, 1H); 6.89 (dd, J=2.2+8.7 HZ, 1H), 6.79 (d, J=2.2 Hz, 1H); 2.58–2.70 (m, 1H); 1.65–1.80 (m, 5H); 1.20–1.35 (m, 5H)];

2-(1,1-dimethylnon-1-yl)-6-hydroxy-4H-chromen-4-one.

C) 2-(1-Adamantyl)-6-hydroxy-4H-thiochromen-4-one a) 1.4 g 4-methoxythiophenol is added to 10 g of polyphosphoric acid preheated to about 90°. Then 2.5 g ethyl 3-(1-adamantyl)-3-oxopropionate is added slowly, and the mixture is stirred for altogether 1.5 hours at 90°. The mixture is poured onto ice/water, vigorously stirred and extracted with ethyl acetate. The combined organic layers are dried over magnesium sulfate and evaporated in vacuo. The residue is purified by chromatography on silica gel (cyclohexane/ethyl acetate 6/1). 2-(1-adamantyl)-6-methoxy-4H-thiochromen-4-one is obtained (colourless crystals; mp 140°). b) Under argon 14 ml of 1M boron tribromide solution in dichloromethane are added at room temperature to a solution of 1.12 g 2-(1-adamantyl)-6-methoxy-4H-thiochromen-4-one in dry dichloromethane. After stirring for 1 hour the mixture is poured onto ice/water and extracted with dichloromethane. The combined organic layers are washed with aqueous sodium bicarbonate solution, dried over magnesium sulfate and evaporated in vacuo. The title compound is obtained (colourless crystals; mp 257° after chromatography on silica gel using cyclohexane/ethyl acetate 4/1 as an eluant).

Analogously the following compound can be prepared: 2t-Butyl-6-hydroxy-4H-thiochromen-4-one (mp 188–190°).

The compounds of formula I in free form or pharmaceutically acceptable salt form, hereinafter briefly named "the agents of the invention", possess pharmaceutical activity. They are indicated for use as pharmaceuticals. In particular, they inhibit steroid sulfatase activity.

Steroidal hormones in particular tissues are associated with several diseases, such as tumors of the breast, endometrium and prostate. Important precursors for the local production of these steroid hormones are steroid 3-O-sulfates which are desulfated by the enzyme steroid sulfatase in the target tissues. Inhibition of this enzyme results in therapeutically relevant, reduced local levels of the corresponding active steroidal hormones. Furthermore, steroid sulfatase inhibitors may also be inmmunosuppressive, and enhance memory when delivered to the brain.

Further, it has now been found that the agents of the invention reduce endogenous levels of androgens and/or estrogens in skin and are thus particularly indicated for use in the treatment of androgen-dependent disorders of the pilosebaceous unit, such as acne, seborrhea, androgenic alopecia and hirsutism, and in the topical treatment of squamous cell carcinoma. Acne is a polyetiological disease caused by interplay of numerous factors, such as inheritance, sebum, hormones, and bacteria. The most important causative factor in acne is sebum production; in almost all acne patients sebaceous glands are larger and produce more sebum than in persons with healthy skin. The development of the sebaceous gland and the extent of sebum production is controlled hormonally by androgens, which play a crucial role in the pathogenesis of acne as well as seborrhea, which is also related to androgen-dependent sebum formation and is important both in initiation and development of acne. Androgenic alopecia is caused by an increased number of hair follicles in the scalp entering the telogen phase and by increased duration of the telogen phase. It is a genetically determined hair loss mediated by androgens in the target tissue. Hirsutism is a pathological thickening and strengthening of hair which is characterized by a masculine pattern of hair growth in children and women. Hirsutism is androgen-induced, either by increased formation of androgens or by increased sensitivity of the hair follicle to androgens.

The agents of the invention are therefore indicated for use as steroid sulfatase inhibitors, particularly in the prevention and treatment of illnesses responsive to steroid sulfatase inhibition, such as illnesses in which the steroid products of sulfatase cleavage play a role, in particular in the prevention and treatment of the following specific conditions: androgen-dependent disorders of the pilosebaceous unit such as acne, seborrhea, androgenic alopecia and hirsutism; cancer, especially estrogen- and androgen-dependent tumors such as tumors of the breast, endometrium and prostate, and squamous cell carcinoma; inflammatory and autoimmune diseases such as rheumatoid arthritis, type I and II diabetes, systemic lupus erythematosus, multiple sclerosis, myastenia gravis, thyroiditis, vasculitis, ulcerative colitis and Crohn's disease; skin disorders such as psoriasis, eczema and contact dermatitis; graft versus host disease; asthma; organ rejection following transplantation; and for enhancement of cognitive function, as in senile dementia, including Alzheimer's disease.

The above activities can be shown e.g. in the following assays (all temperatures are in degrees Celsius):

1. Steroid Sulfatase Inhibition in vitro a) Purification of Human Steroid Sulfatase Human placenta is obtained fresh after delivery and stripped of membranes and connective tissues. For storage the material is frozen at −70°. After thawing, all further steps are carried out at 4°, while pH values are adjusted at 20°. 400 g of tissue are homogenized in 1.2 l of buffer A (50 mM Tris-HCl, pH 7.4; 0.25M sucrose). The homogenate is centrifuged at 10,000 g for 45 minutes. The supernatant is set aside and the pellet re-homogenized in 500 ml of buffer A. After centrifugation the two supernatants are combined and subjected to ultracentrifugation (100,000 g, 1 hour). The pellet is resuspended in buffer A and the centrifugation repeated. The pellet is suspended in 50 ml of 50 mM Tris-HCl, pH 7.4 and stored at −20° until further work-up.

After thawing, microsomes are collected by ultracentrifugation as described above and suspended in 50 ml of buffer B (10 mM Tris-HCl, pH 7.0; 1 mM EDTA; 2 mM 2-mercaptoethanol; 1% Triton X-100 v/v; 0.1% aprotinin v/v). After 1 hour on ice with gentle agitation the suspension is centrifuged (100,000 g, 1 hour). The supernatant containing the enzyme activity is collected and the pH adjusted to 8.0 with 1M Tris.

Then the solution is applied to a hydroxyapatite column (2.6×20 cm) equilibrated with buffer B, pH 8.0. The column is washed with buffer B at a flow rate of 2 ml/min. The activity is recovered in the flow-through. The pool is adjusted to pH 7.4 and subjected to chromatography on a concanavalin-A sepharose column (1.6×10 cm) equilibrated in buffer C (20 mM Tris-HCl, pH 7.4; 0.1% Titon X-100 v/v; 0.5 M NaCl), The column is washed with buffer C and then the bound protein eluted with 10% v/v methyl mannoside in buffer C. Active fractions are pooled and dialysed against buffer D (20 mM Tris-HCl, pH 8.0; 1 mm EDTA; 0.1% Triton X-100 v/v; 10% glycerol v/v).

The active fractions are applied to a blue sepharose column (0.8×10 cm) equilibrated with buffer D; the column is washed and then eluted with a linear gradient of buffer D to 2M NaCl in buffer D. Active fractions are pooled, concentrated as required (Centricon 10), dialysed against buffer D and stored in aliquots at −20°.

b) Assay

Purified human steroid sulfatase also readily cleaves aryl sulfates such as 4-methylumbelliferyl sulfate. Assay mixtures are prepared by consecutively dispensing the following solutions into the wells of white microtiter plates:

1) 50 μl of substrate solution (1.5 mM 4-methylumbelliferyl sulfate in 0.1 M Tris-HCl, pH 7.5) (final concentration 0.5 mM);

2) 50 μl of diluted test compound solution diluted in 0.1 M Tris-HCl, pH 7.5, 0.1% Triton X-100 v/v (stock solutions of the test compounds are prepared in dimethylsulfoxide; final concentrations of the solvent in the assay mixture do not exceed 1%);

3) 50 μl of enzyme solution (approximately 12 U/ml) (one enzyme unit U is the amount of steroid sulfatase that hydrolyses 1 nmol of 4-methylumbelliferyl sulfate per hour at an initial substrate concentration of 500 μM in 0.1M Tris-HCl, pH 7.5; 0.1% Triton X-100 v/v; at 37°).

Plates are incubated at 37° for 1 hour. The reaction is then stopped by addition of 100 μl of 0.2M NaOH. Fluorescence intensity is measured (Titertek Fluoroskan II) with $\lambda_{ex}$=355 nm and $\lambda_{em}$=460 nm.

c) Computation of Relative $IC_{50}$ Values

From the fluorescence intensity (I) obtained at different concentrations (c) of test compound the concentration inhibiting the enzymatic activity by 50% ($IC_{50}$) is calculated using the relation $$I = \frac{I_{100}}{1 + (c/IC_{50})^s}$$

where $I_{100}$ is the intensity observed in the absence of inhibitor and s is the slope factor.

Estrone-3-O-sulfamate serves as reference compound and its $IC_{50}$ value is determined in parallel to the test compounds and is about 60 nM. Relative $IC_{50}$ values (rel $IC_{50}$) are defined as follows:

$$\text{rel } IC_{50} = \frac{IC_{50} \text{ of test compound}}{IC_{50} \text{ of estrone sulfamate}}$$

The agents of the invention inhibit steroid sulfatase in this assay with rel $IC_{50}$ values in the range of 0.006 to 30.

2. Steroid Sulfatase Inhibition in Cell Extracts

Human keratinocytes (HaCaT) or human skin-derived fibroblasts (1BR3GN) are grown to confluency using standard cell culture techniques. Cells are harvested by trypsinization, washed once with phosphate-buffered saline (PBS) and suspended in 20 mM Tris-HCl, pH 8.0. The suspension is sonicated and then centrifuged at 12000 g for 30 minutes. The supernatant is subjected to ultracentrifugation at 100000 g for 60 minutes. The resulting microsomal pellet is resuspended in buffer containing 0.1% Triton X-100 v/v and left standing for 30 minutes. After additional centrifugation at 100000 g for 30 minutes the supernatant which contains the solubilized enzyme is removed and stored at 4°.

For assay of the enzymatic activity 10 μl of enzyme solution are added to 100 μl of 50 μM dehydroepiandrosterone sulfate (DHEAS) containing approximately 60000 dpm [$^3$H]-DHEAS (21 Ci/mmol) in 0.1 M Tris-HCl, pH 7.5; 0.1% v/v Triton X-100. Test compound is included at various concentrations added from stock solutions in DMSO. After incubation for 30 minutes at 37°, 250 μl of 1N NaOH are added. The mixture is extracted with 1 ml of toluene. 800 μl of the organic layer are subjected to liquid scintillation counting to determine the fraction of substrate that has been cleaved to dehydroepiandrosterone (DHEA). $IC_{50}$ values are computed as described above. The $IC_{50}$ of estrone sulfamate for steroid sulfatase inhibition is in the range of about 1–5 nM, depending on the enzyme concentration used.

The agents of the invention inhibit steroid sulfatase activity in HaCaT keratinocytes and 1BR3GN fibroblasts with rel $IC_{50}$ values in the range of 0.006 to 50.

3. Steroid Sulfatase Inhibition in HaCaT Cells Incubated with DHEAS

HaCaT keratinocytes are cultivated in Dulbecco's modification of Eagle's medium (DMEM) supplemented with 10% v/v fetal calf serum (FCS). They are grown to confluency and then harvested by trypsinization. Approximately $2 \times 10^6$ cells are dispensed into 9.6 cm$^2$ dishes and incubated in medium containing FCS until confluency is reached. Then the medium is changed to serum-free DMEM (1.5 ml per well); 0.3 μM DHEAS is included as substrate with 1.5 μCi/well [$^3$H]-DHEAS (21 Ci/mmol) as tracer. Incubation is continued for 96 hours. Test compound is added from stock solutions in ethanol; the final ethanol concentration in the assay does not exceed 1% v/v. In parallel, DHEAS is also incubated with medium without cells as a control for non-enzymatic hydrolysis. After incubation, the supernatant is removed and 1 ml is extracted with 4 ml of toluene. 3 ml of the organic layer are collected and the solvent evaporated in vacuo. The residue is taken up in acetonitrile. 10 μg DHEA is included as carrier. The extract is analysed by high performance liquid chromatography (HPLC) using a RP C-8 column and isocratic elution with 10 mM ammonium sulfate pH 6/acetonitrile (60/40), at a flow rate of 1 ml/min. The amount of DHEA cleaved during incubation is calculated from the area of the corresponding radioactive peak determined by continuous monitoring with a radiodetector equipped with a flow-cell. From the data obtained at various concentrations of test compound, $IC_{50}$ and rel $IC_{50}$ values are calculated as described above for assay 1. The $IC_{50}$ value for estrone sulfamate is approximately 0.1 nM.

The agents of the invention show rel $IC_{50}$ values in this assay in the range of 0.1 to 100.

For the above uses the dosage to be used will vary, of course, depending e.g. on the particular agent employed, the mode of administration and the treatment desired. However, in general, satisfactory results are obtained when the agents are administered at a daily dosage of from about 0.1 mg/kg to about 100 mg/kg animal body weight, suitably given in divided doses two to four times daily. For most large mammals the total daily dosage is from about 5 mg to about 5000 mg, conveniently administered, for example, in divided doses up to four times a day or in retard form. Unit dosage forms comprise, for example, from about 1.25 mg to about 2500 mg of the compounds in admixture with at least one solid or liquid pharmaceutically acceptable carrier or diluent.

The agents of the invention may be administered in similar manner to known standards for use in such indications. The agents may be admixed with conventional chemotherapeutically acceptable carriers and diluents and, optionally, further excipients, and administered e.g. orally in such forms as tablets and capsules.

Alternatively, the agents may be administered topically in such conventional forms as lotions, solutions, ointments and creams, parenterally or intravenously. The concentration of active substance will, of course, vary depending e.g. on the particular agent employed, the treatment desired and the nature of the form. In general, however, satisfactory results are obtained in e.g. topical application forms at concentrations of from about 0.05% to about 5%, particularly from about 0.1% to about 1% by weight.

Pharmaceutical compositions comprising an agent of the invention together with at least one pharmaceutically acceptable carrier or diluent also form part of the invention, as well as a process for the preparation thereof by mixing an agent of the invention together with at least one pharmaceutically acceptable carrier or diluent. The invention also comprises the agents of the invention for use as pharmaceuticals, especially as steroid sulfatase inhibitors, particularly in the prevention or treatment of illnesses responsive to steroid sulfatase inhibition, such as illnesses in which the steroid products of sulfatase cleavage play a role, in particular in the prevention and treatment of the specific conditions indicated above. It further comprises the agents of the invention for use in the preparation of a medicament for use as steroid sulfatase inhibitor.

The invention particularly includes the agents of the invention for use in the treatment of androgen-dependent disorders of the pilosebaceous unit, such as acne, seborrhea, androgenic alopecia and hirsutism, or in the topical treatment of squamous cell carcinoma, as well as the agents of the invention for use in the preparation of a medicament for use in the treatment of androgen-dependent disorders of the pilosebaceous unit or in the topical treatment of squamous cell carcinoma.

The invention further concerns a method for the prophylactic or curative treatment of illnesses responsive to steroid sulfatase inhibition, such as illnesses in which the steroid products of sulfatase cleavage play a role, in particular in the prevention and treatment of the specific conditions indicated above, which comprises administering a therapeutically effective amount of an agent of the invention to a subject in need of such treatment.

The compounds of Example 1, 2-t-butyl-4H-chromen-4-one-6-O-sulfamate, of Example 9, 2-(1-adamantyl)-4H-chromen-4-one-6-O-sulfamate, and of Example 22, 2-(1-adamantyl)-4H-thiochromen-4-one-6-O-sulfamate, especially the compound of Example 1, are the most preferred agents of the invention in these indications. It has, for example, been determined that in the above assay 1. these agents have a rel $IC_{50}$ value of about 0.4, 0.1 and 0.0064, respectively.

What is claimed is:

1. A compound of formula I

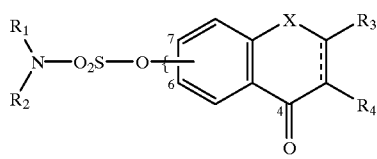

wherein
$R_1$ and $R_2$ independently are hydrogen, acyl, alkoxycarbonyl or alkyl;
either the sulfamoyloxy side chain is bound to the 6 position;
$R_3$ is alkyl; alkenyl; alkinyl; a cycloalkyl moiety optionally substituted by alkyl, alkoxy or halogen; arylalkenyl; arylalkinyl; acyl; cycloalkylalkyl; 3-oxo-2-oxacamphanyl; or is 6,6-dimethylbicyclo[3.1.1]hept-2-en-2-yl; and
$R_4$ is hydrogen; alkyl; hydroxy; or alkoxy;
or the sulfamoyloxy side chain is bound to the 7 position;
$R_3$ has the significance indicated above for $R_4$; and $R_4$ has the significance indicated above for $R_3$;
X is O or S; and the symbol --- is a single or a double bond;
in free form or salt form.

2. A compound according to claim 1 of formula Ip

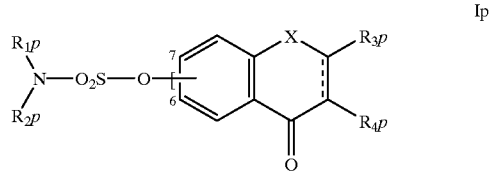

wherein
$R_{1p}$ and $R_{2p}$ independently are hydrogen or alkyl;
either the sulfamoyloxy side chain is bound to the 6 position,
$R_{3p}$ with the exception of 3-oxo-2-oxacamphanyl has the significance indicated in claim 1 for $R_3$, and
$R_{4p}$ is hydrogen;
or the sulfamoyloxy side chain is bound to the 7 position,
$R_{3p}$ is hydrogen, and
$R_{4p}$ with the exception of 3-oxo-2-oxacamphanyl has the significance indicated in claim 1 for $R_3$; and
X and the the symbol --- are as defined in claim 1;
in free form or salt form.

3. A compound according to claim 1 of formula Is

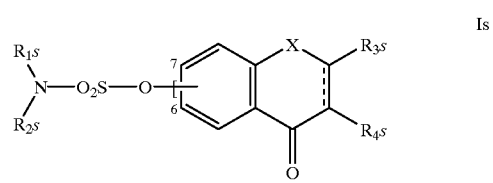

wherein
$R_{1s}$ is hydrogen, methyl, acetyl or methoxycarbonyl;
$R_{2s}$ is hydrogen or methyl;
either the sulfamoyloxy side chain is bound to the 6 position,
$R_{3s}$ is alkyl of 1 to 12 carbon atoms; a monocyclic cycloalkyl moiety of 3 to 12 carbon atoms optionally substituted by methyl; 1-adamantyl; nor-adamantyl; 4-pentylbicyclo[2.2.2]oct-1-yl; 2-phenylethenyl; bicyclo[2.2.1]hept-2-ylmethyl; 3-oxo-2-oxacamphanyl; or 6,6-dimethylbicyclo[3.1.1]hept-2-en-2-yl, and
$R_{4s}$ is hydrogen;
or the sulfamoyloxy side chain is bound to the 7 position,
$R_{3s}$ is hydrogen, and
$R_{4s}$ is cycloalkyl of 5 to 7 carbon atoms; and
X and the symbol --- are as defined in claim 1;
in free form or salt form.

4. 2-t-butyl-4H-chromen-4-one-6-O-sulfamate in free form or salt form.

5. 2-(1-adamantyl)-4H-chromen-4-one-6-O-sulfamate or 2-(1-adamantyl)-4H-thiochromen-4-one-6-O-sulfamate, in free form or salt form.

6. A process for the preparation of a compound according to claim 1 comprising a) sulfamoylating a compound of formula II

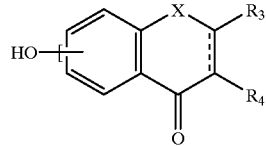

II wherein $R_3$, $R_4$, X and the symbol - - - are as defined in claim 1; or b) for the preparation of a compound of formula Ia

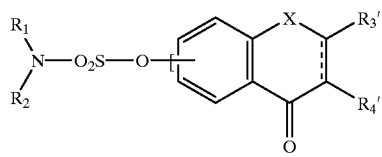

Ia wherein

X, $R_1$, $R_2$ and the symbol - - - are as defined in claim 1 and $R_3'$ and $R_4'$ with the exception of alkenyl, alkinyl, arylalkenyl, arylalkinyl and 6,6-dimethylbicyclo[3.1.1]hept-2-en-2-yl have the significance indicated in claim 1 for, respectively, $R_3$ and $R_4$, reducing a corresponding compound of formula Ib

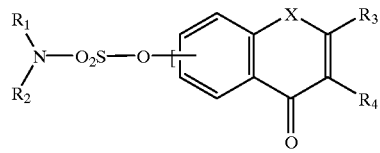

Ib wherein the substituents are as defined in claim 1; or c) for the preparation of a compound of formula I as defined in claim 1 and wherein at least one of $R_1$ and $R_2$ is alkyl, acyl or alkoxycarbonyl, N-substituting a compound of formula I wherein at least one of the substituents $R_1$ and $R_2$ is hydrogen;

and recovering the resultant compound of formula I in free form or salt form.

7. A pharmaceutical composition comprising a compound according to claim 1 in free form or pharmaceutically acceptable salt form together with at least one pharmaceutically acceptable carrier or diluent.

8. A method of treatment of illnesses responsive to steroid sulfatase inhibition which comprises administering a therapeutically effective amount of a compound according to claim 1 in free form or pharmaceutically acceptable salt form to a subject in need of such treatment.

9. A method of treatment of androgen-dependent disorders of the pilosebaceous unit or in the topical treatment of squamous cell carcinoma, comprising administering a therapeutically effective amount of compound according to claim 1 in free form or pharmaceutically acceptable salt form to a subject in need of such treatment.

* * * * *

UNITED STATES PATENT AND TRADEMARK OFFICE
CERTIFICATE OF CORRECTION

PATENT NO. : 6,346,626 B1
DATED : February 12, 2002
INVENTOR(S) : Billich et al.

It is certified that error appears in the above-identified patent and that said Letters Patent is hereby corrected as shown below:

Title page,
Item [30], should read -- Foreign Application Priority Data
April 9, 1998 (GB) ....................9807779 --

Column 12,
Line 47, should read -- buffer D (20 mM Tris-HCl, pH 8.0; 1 mM EDTA; 0.1% --

Signed and Sealed this

Twenty-second Day of October, 2002

Attest:

Attesting Officer

JAMES E. ROGAN
*Director of the United States Patent and Trademark Office*